United States Patent [19]

Takemori et al.

[11] Patent Number: 5,171,570
[45] Date of Patent: Dec. 15, 1992

[54] SUBSTANCE HAVING SUPPRESSING FUNCTION FOR DISEASES RELATING TO INCREASE IN CHOLESTEROL, AND FOODS AND DRINKS IN WHICH IT IS USED

[75] Inventors: Toshio Takemori, Tokyo; Toshinobu Tsurumi, Okegawa; Masahiro Takagi, Matsudo; Tatsuya Kamiwaki, Kawagoe, all of Japan

[73] Assignee: Lotte Company Limited, Tokyo, Japan

[21] Appl. No.: 623,545

[22] Filed: Dec. 7, 1990

[30] Foreign Application Priority Data

Dec. 8, 1989 [JP] Japan .................. 1-317798
Dec. 8, 1989 [JP] Japan .................. 1-317799
Dec. 8, 1989 [JP] Japan .................. 1-317800

[51] Int. Cl.$^5$ ............................................. A61K 35/78
[52] U.S. Cl. .................................................. 424/195.1
[58] Field of Search ...................................... 424/195.1

[56] References Cited

PUBLICATIONS

H. Fukaba et al., J. Jap. Soc. Natr. and Food Sci. 42:449-459, 1989.
CA 94: 71475k JA Kokai Tokkyo Koho 80,141,415, Nov. 5, 1980.
CA 112: 117376 Fukuba et al. (1989).
The Merck Index, Windholz et al. (1983) 10th Ed. p. 5320.
Bakery Production & Marketing vol. 25 p. 36(7) Jan. 24 (1990).

*Primary Examiner*—John W. Rollins
*Attorney, Agent, or Firm*—Young & Thompson

[57] ABSTRACT

There are disclosed substances having suppressing function for diseases relating to increase in cholesterol in animal and human bodies wherein they are obtained as an acid-insoluble fraction containing lignin which is a phenolic polymer compound extracted from wood material as a main component. The substances are a substance having suppressing function for increase in blood cholesterol, a substance having suppressing function for increase in blood pressure, and a substance having suppressing function for the cholesterol gallstone formation. There are also disclosed foods and drinks in which the above mentioned substances are contained having suppressing function for diseases relating to increase in cholesterol in animal and human bodies.

10 Claims, No Drawings

SUBSTANCE HAVING SUPPRESSING FUNCTION FOR DISEASES RELATING TO INCREASE IN CHOLESTEROL, AND FOODS AND DRINKS IN WHICH IT IS USED

FIELD OF THE INVENTION

The present invention relates to substances having suppressing function for diseases relating to increase in cholesterol in animal and human bodies and foods and drinks in which they are contained having suppressing function for diseases relating to increase in cholesterol in animal and human bodies.

The present invention relates to a substance having suppressing function for increase in blood cholesterol and foods and drinks in which it is used, in particular relates to a substance having suppressing function for increase in blood cholesterol and foods and drinks in which it is used which are prepared from an albumen (including cocoa powder and the like) and/or an outer peel of cacao bean exactly as they are, or those after addition of physicochemical treatment or biochemical pre-treatment with respect to them.

The present invention relates to a substance having suppressing function for increase in blood pressure and foods and drinks in which it is used, in particular relates to a substance having suppressing function for increase in blood pressure and foods and drinks in which it is used which are prepared from cacao (including an albumen, an outer peel, and cocoa powder after processing them) or other plant bodies (wood pulp, wood powder, straw, chaff, bran, bagasse and the like) exactly as they are, or those after addition of physicochemical treatment or biochemical pre-treatment with respect to them.

The present invention relates to a substance having suppressing function for cholesterol gallstone formation and foods and drinks in which it is used, in particular relates to a substance having suppressing function for cholesterol gallstone formation and foods and drinks in which it is used which are prepared from cacao (including an albumen, an outer peel, and cocoa powder after processing them) or other plant bodies (wood pulp, wood powder, straw, chaff, bran, bagasse and the like) exactly as they are, or those after addition of physicochemical treatment or biochemical pre-treatment with respect to them.

BACKGROUND OF THE INVENTION

According to results of various epidemiological research, it has become evident that when blood total cholesterol is high, the expression ratio of the atherosclerosis and the ischemic heart disease becomes high. In the present age which is so-called as the food-saturated age, we are apt to fall into such a tendency that sufficient meals containing high protein, high fat, and a few dietary fibre are eaten without vigorous labor and exercise. This makes the mechanism for controlling cholesterol irregular, resulting in increase in the cholesteremia.

As food raw materials for decreasing cholesterol are known unsaturated fatty acids in vegetable oil (those of n-6), unsaturated fatty acids in fish oil (those of n-3, EPA and DHA), taurine contained in fishery products, and water-soluble dietary fibre such as pectin and the like. The main component of LG of the present invention is generally called as lignin, which is a phenolic substance of the polymer type scarcely soluble in water. It is common to pectin and alginic acid in that they are polymer compounds, however, they are highly hygroscopic to have viscosity after dissolving in water as compared with LG, so that it has been difficult to add in a large amount as a food raw material from a view of stability of food.

Namely, there have been such disadvantages that polymer compounds such as pectin and alginic acid are highly hygroscopic to have viscosity after dissolving in water, so that it is difficult to add in a large amount as a food raw material from a view of stability of food, and the natural product of taurine requires high cost, and the unsaturated fatty acids provide high calorie. Therefore, development has been waited for a material especially of the polymer type which does not damage the property of food and is capable of adding in a relatively large amount.

Brain blood vessel diseases, which have been the first in the ranking of death classified by the cause of death in Japan from 1951 to 1980, are in a decreasing tendency, however, accompanying with the change in eating habits, there have appeared increase in the arterial sclerosis and the hypertension as well as a tendency of becoming younger thereof, and the disease structure is also going to become near to the United States and European countries.

It is the hypertension that is listed as the first in the causing factor as a dangerous factor of brain blood vessel diseases and the ischemic heart disease, and for countermeasures therefor, there is considerable interest not only in Japan but also in the United States and European countries.

Blood pressure is said to be determined by a complex interaction between genetic factors and environmental factors. As the environmental factors are considered various factors such as life environment, cool atmosphere, smoking, nutrition and the like, and the most important is considered to be the excess intake of common salt. The intake amount of common salt is much in Japan, and a harmful influence of excess intake has been discussed, and in the necessary amount of nutrition for Japanese people established in 1979 is shown a suitable amount of common salt to be not more than 10 g per day, however, intake of 12 g or more or less is carried out as an average of whole country in the present circumstances.

From a view of removing intake common salt from a body by means of chemical absorption, such a trial has been already proposed that an artificial cation exchange resin such as an amberlite is medically utilized to use in medical treatments for hypertension, however, it has been difficult to give medication continuously. In addition, from another view than the removal of common salt by the chemical absorption, suppression of increase in blood pressure in a rat has been reported by using potassium alginate and calcium alginate which are one of the dietary fibre, however they cannot be used as a food raw material. Thus, development of a raw material which does not damage the property of food and can be added continuously has been waited.

Recently, calculuses generated in various organs have become problems. Among them, the gall bladder has the highest generation frequency. The gallstone is formed by deposition of bile components to be a calculus during excretion to the duodenum via the hepatobile duct, the cystic duct and the choledoch duct. At present, in the case of Japanese aged people, one person among 20 persons of male and one person among 10 persons of female have a gallstone. Before the Second World War, the pigment calculus occupied most parts, however, accompanying with the change of eating habits to be those in the United States and European countries, the pigment calculus has decreased, instead thereof, the cholesterol gallstone is in a tendency of rapid increase, which is considered to further increase in future.

As medical treatment methods for the gallstone, according to a rough classification, there are those of the internal medicine and the surgery. As those of the internal medicine are utilized a choleretic agent (a bile acid agent, a Curcuma agent, synthetic substances and the like), a bile excretion agent (calcium sulfate, an artificial culculus source salt) as a bile activating agent, and there are those in which as a gallstone-dissolving agent are used kenodeoxycholate and ursodeoxycholate, which are only an assistant medical treatment method at the present stage. And the medical treatment methods of the surgery also have problems in that there is possibility to cause combined diseases, and it is difficult to determin the timing for an operation and the like. According to the above, at present studies are carried out from both sides of the medical treatment and the prevention.

As preventing methods for the gallstone, taking the fact that the gallstone is formed on account of excess saturation of cholesterol into consideration, the excess saturation of cholesterol is avoided, that is the cholesterol level may be made not to increase. For this, the dietary cholesterol may be decreased, however, it is fairly difficult in the present differentiation in foods and the style of eating. Thus, it results in being preferable that a food component having a function for decreasing cholesterol may be utilized.

SUMMARY OF THE INVENTION

It has now been found out as the result of study of components in cacao from various aspects that a residue of sulfuric acid hydrolysis which is an acid-insoluble fraction (LG-A1) and an alkaline extraction fraction (LG-A2) belonging to a phenolic polymer fraction containing lignin as a main component (hereifafter referred to as LG) have suppressing function for increase in blood cholesterol.

Thus the object of the present invention is to provide a substance having suppressing function for increase in blood cholesterol and foods and drinks in which it is used having function for decreasing blood cholesterol which are prepared from an albumen (including cocoa powder and the like) and/or an outer peel of cacao bean exactly as they are, or those after addition of physicochemical treatment or biochemical treatment, which are a substance and foods and drinks in which it is used giving no damage to the property of food and being capable of adding in a relatively large amount.

It has now been found out as the result of study of components in cacao bean and other plant bodies (wood pulp, wood powder, straw, chaff, bran, bagasse and the like) from various aspects that a residue of sulfuric acid hydrolysis which is an acid-insoluble fraction (LG-B1) and an alkaline extraction fraction (LG-B2) both of which contain lignin as a main component absorb sodium ion, and further found out that they have suppressing function for increase in blood pressure.

Thus the object of the present invention is to provide a substance having suppressing function for increase in blood pressure and foods and drinks in which it is used having function for decreasing blood pressure which are prepared from cacao (including an albumen, an outer peel, and cocoa powder after processing them) or other plant bodies (wood pulp, wood powder, straw, chaff, bran, bagasse and the like) exactly as they are, or those after addition of physicochemical treatment or biochemical treatment, which are a substance and foods and drinks in which it is used giving no damage to the property of food and being capable of adding continuously.

It has now been found out as the result of study of components in cacao (including an albumen, an outer peel, and cocoa powder after processing them) or other plant bodies (wood pulp, wood powder, straw, chaff, bran, bagasse and the like) from various aspects that a residue of sulfuric acid hydrolysis which is an acid-insoluble fraction (LG-C1) and an alkaline extraction fraction (LG-C2) which belong to a phenolic polymer fraction containing lignin as a main component (LG) have suppressing function for cholesterol gallstone formation.

Thus the object of the present invention is to provide a substance having suppressing function for cholesterol gallstone formation and foods and drinks in which it is used having suppressing function for cholesterol gallstone formation which are prepared from cacao (including an albumen, an outer peel, and cocoa powder after processing them) or other plant bodies (wood pulp, wood powder, straw, chaff, bran, bagasse and the like) exactly as they are, or those after addition of physicochemical treatment or biochemical treatment, which are a substance and foods and drinks in which it is used giving no damage to the property of food and being capable of adding in a relatively large amount.

According to the present invention, there is provided a substance having suppressing function for diseases relating to increase in cholesterol in animal and human bodies wherein it is obtained as an acid-insoluble fraction containing lignin which is a phenolic polymer compound extracted from wood materials as a main component.

PREFERRED EMBODIMENT OF THE INVENTION

According to the present invention, there is provided a substance having suppressing function for increase in blood cholesterol characterized in that it is obtained as an acid-insoluble fraction containing lignin which is a phenolic polymer compound extracted from wood materials as a main component.

Alternatively, according to the present invention, there is provided an LG-A1 substance which is a substance having suppressing function for increase in blood cholesterol containing lignin which is a phenolic polymer compound as a main component, being obtained as a residue using an albumen (including cocoa powder and the like) and/or an outer peel of cacao bean as a material exactly as they are, or those after addition of physical treatment such as grinding, milling, heating, boiling with steam, or grinding by explosion, chemical treatment such as extraction with various solvents (such as hexane, acetone, ethanol and the like), or biochemical treatment such as fermentation or enzyme treatment (such as protease, amylase and the like) with respect to them as a material, and adding sulfuric acid of a concentration of 40 to 98% to the material by a volume of 2 to 10 times to hydrolyze to perform filtration and washing, characterized in that it has following physicochemical characteristics:
molecular weight: not less than 200,
sugar portion: not more than 1%,
nitrogen content: 1.5 to 5.5%,
fat portion: not more than 10%,
ash portion: not more than 10%,
methoxyl content: 5 to 40%.

In addition, the numerical values for sugar, crude protein, fat portion, and ash portion are those according to a general analysis.

Alternatively, according to the present invention there are provided foods and drinks having suppressing function for increase in blood cholesterol characterized in that they contain the above mentioned LG-A1 substance as an active component by adding during usual production of foods.

Alternatively, according to the present invention, there is provided an LG-A2 substance which is a substance having suppressing function for increase in blood cholesterol containing lignin which is a phenolic polymer compound as a main component, being obtained as a precipitate using
an albumen (including cocoa powder and the like) and/or an outer peel of cacao bean as a material exactly as they are, or
those after addition of physical treatment such as grinding, milling, heating, boiling with steam, or grinding by explosion, chemical treatment such as extraction with various solvents (such as hexane, acetone, ethanol and the like), or biochemical treatment such as fermentation or enzyme treatment (such as protease, amylase and the like) with respect to them as a material, and
adding sodium hydroxide or potassium hydroxide of a concentration of 0.1 to 2.0% to the material by a volume of 10 to 50 times, performing extraction for not less than 30 minutes at room temperature or with heating, neutralizing extracted liquid with hydrochloric acid to be not more than pH 7 to allow the precipitate to generate, and further taking out by a means such as centrifugation or filtration to perform washing with distilled water, characterized in that
it has following physicochemical characteristics:
molecular weight: not less than 200,
sugar portion: not more than 1%,
nitrogen content: 1.5 to 5.5%,
fat portion: not more than 10%,
ash portion: not more than 10%,
methoxyl content: 5 to 40%.

In addition, the numerical values for sugar, crude protein, fat portion, and ash portion are those according to a general analysis.

Alternatively, according to the present invention, there are provided foods and drinks having suppressing function for increase in blood cholesterol characterized in that they contain the above mentioned LG-A2 substance as an active component by adding during usual production of foods.

According to the present invention, there is provided a substance having suppressing function for increase in blood pressure characterized in that it is obtained as an acid-insoluble fraction containing lignin which is a phenolic polymer compound extracted from wood materials as a main component.

Alternatively, according to the present invention, there is provided an LG-B1 substance which is a substance having suppressing function for increase in blood pressure containing lignin which is a phenolic polymer compound having high cation exchange capacity to absorb sodium ion as a main component, being obtained as a residue using
cacao (including an albumen, an outer peel, and cocoa powder after processing them) or other plant bodies (wood pulp, wood powder, straw, chaff, bran, bagasse and the like) as a material exactly as they are, or
those after addition of physical treatment such as grinding, milling, heating, boiling with steam, or grinding by explosion, chemical treatment such as extraction with various solvents (such as hexane, acetone, ethanol and the like), or biochemical treatment such as fermentation or enzyme treatment (such as protease, amylase and the like) with respect to them as a material, and
adding sulfuric acid of a concentration of 40 to 98% to the material by a volume of 2 to 10 times to hydrolyze to perform filtration and washing, characterized in that
it has following physiocochemical characteristics:
molecular weight: not less than 200,
sugar portion: not more than 1%,
nitrogen content: 1.5 to 5.5%,
fat portion: not more than 10%,
ash portion: not more than 10%,
methoxyl content: 5 to 40%.

In addition, the numerical values for sugar, crude protein, fat portion, and ash portion are those according to a general analysis.

Alternatively, according to the present invention there are provided foods and drinks having suppressing function for increase in blood pressure characterized in that they contain the above mentioned LG-B1 substance as an active component by adding during usual production of foods.

Alternatively, according to the present invention, there is provided an LG-B2 substance which is a substance having suppressing function for increase in blood pressure containing lignin which is a phenolic polymer compound having high cation exchange capacity to absorb sodium ion as a main component, being obtained as a precipitate using
cacao (including an albumen, an outer peel, and cocoa powder after processing them) or other plant bodies (wood pulp, wood powder, straw, chaff, bran, bagasse and the like) as a material exactly as they are, or
those after addition of physical treatment such as grinding, milling, heating, boiling with steam, or grinding by explosion, chemical treatment such as extraction with various solvents (such as hexane, acetone, ethanol and the like), or biochemical treatment such as fermentation or enzyme treatment (such as protease, amylase and the like) with respect to them as a material, and
adding sodium hydroxide or potassium hydroxide of a concentration of 0.1 to 2.0% to the material by a volume of 10 to 50 times, performing extraction for not less than 30 minutes at room temperature or with heating, neutralizing extracted liquid with hydrochloric acid to be not more than pH 7 to allow the precipitate to generate, and further taking out by a means such as centrifugation or filtration to perform washing with distilled water, characterized in that
it has following physicochemical characteristics:

molecular weight: not less than 200,
sugar portion: not more than 1%,
nitrogen content: 1.5 to 5.5%,
fat portion: not more than 10%,
ash portion: not more than 10%,
methoxyl content: 5 to 40%.

In addition, the numerical values for sugar, crude protein, fat portion, and ash portion are those according to a general analysis.

Alternatively, according to the present invention, there are provided foods and drinks having suppressing function for increase in blood pressure characterized in that they contain the above mentioned LG-B2 substance as an active component by adding during usual production of foods.

According to the present invention, there is provided a substance having suppressing function for cholesterol gallstone formation characterized in that it is obtained as an acid-insoluble fraction containing lignin which is a phenolic polymer compound extracted from wood materials as a main component.

Alternatively, according to the present invention, there is provided an LG-C1 substance which is a substance having suppressing function for cholesterol gallstone formation containing lignin which is a phenolic polymer compound as a main component, being obtained as a residue using cacao (including an albumen, an outer peel, and cocoa powder after processing them) or other plant bodies (wood pulp, wood powder, straw, chaff, bran, bagasse and the like) as a material exactly as they are, or those after addition of physical treatment such as grinding, milling, heating, boiling with steam, or grinding by explosion, chemical treatment such as extraction with various solvents (such as hexane, acetone, ethanol and the like), or biochemical treatment such as fermentation or enzyme treatment (such as protease, amylase and the like) with respect to them as a material, and adding sulfuric acid of a concentration of 40 to 98% to the material by a volume of 2 to 10 times to hydrolyze to perform filtration and washing, characterized in that it has following physicochemical characteristics:
molecular weight: not less than 200,
sugar portion: not more than 1%,
nitrogen content: 1.5 to 5.5%,
fat portion: not more than 10%,
ash portion: not more than 10%,
methoxyl content: 5 to 40%.

In addition, the numerical values for sugar, crude protein, fat portion, and ash portion are those according to a general analysis.

Alternatively, according to the present invention there are provided foods and drinks having suppressing function for cholesterol gallstone formation characterized in that they contain the above mentioned LG-C1 substance as an active component by adding during usual production of foods.

Alternatively, according to the present invention, there is provided an LG-C2 substance which is a substance having suppressing function for cholesterol gallstone formation containing lignin which is a phenolic polymer compound as a main component, being obtained as a precipitate using cacao (including an albumen, an outer peel, and cocoa powder after processing them) or other plant bodies (wood pulp, wood powder, straw, chaff, bran, bagasse and the like) as a material exactly as they are, or those after addition of physical treatment such as grinding, milling, heating, boiling with steam, or grinding by explosion, chemical treatment such as extraction with various solvents (such as hexane, acetone, ethanol and the like), or biochemical treatment such as fermentation or enzyme treatment (such as protease, amylase and the like) with respect to them as a material, and adding sodium hydroxide or potassium hydroxide of a concentration of 0.1 to 2.0% to the material by a volume of 10 to 50 times, performing extraction for not less than 30 minutes at room temperature or with heating, neutralizing extracted liquid with hydrochloric acid to be not more than pH 7 to allow the precipitate to generate, and further taking out by a means such as centrifugation or filtration to perform washing with distilled water, characterized in that it has following physicochemical characteristics:
molecular weight: not less than 200,
sugar portion: not more than 1%,
nitrogen content: 1.5 to 5.5%,
fat portion: not more than 10%,
ash portion: not more than 10%,
methoxyl content: 5 to 40%.

In addition, the numerical values for sugar, crude protein, fat portion, and ash portion are those according to a general analysis.

Alternatively, according to the present invention, there are provided foods and drinks having suppressing function for cholesterol gallstone formation characterized in that they contain the above mentioned LG-C2 substance as an active component by adding during usual production of foods.

Both of the LG-A1 and the LG-A2 according to the present invention are the acid-insoluble fraction extracted from wood materials, which have such a common characteristic that they contain lignin which is a phenolic polymer compound as a main component, so that they can be generally called as the LG fraction.

Cholesterol plays important roles in living bodies in such a way that it serves as a material for hormone, a composition for biomembrane and the like, which is not a useless bad one as such. However, in eating habits in the present age, it becomes a problem to take excess chlesterol.

In order to solve the above, the present invention has been completed by seeking for in cacao a substance which can improve chloesterol concentration in blood to find out the LG's. These have no limit for addition because the material is a natural food raw material, in addition, the main component thereof is considered to be lignin which is the dietary fibre, having added value of scarcely hydroscopic property that is low calorie.

The main component of the LG disclosed by the present invention is one generally called as lignin, which is a phenolic substance difficult to dissolve in water. It is common to pectin and alginic acid in that they are polymer compounds, however, they are highly hygroscopic to have viscosity after dissolving in water as compared with the LG, so that addition in a large amount as a food raw material is difficult from a view of stability of food.

The LG disclosed by the present invention is one, the material of which is a natural food raw material having no limit for the amount of addition, which also has no hygroscopic property to be easy to add in a large amount to food from a view of food science.

In addition, especially the outer peel of cacao is produced in a large amount as a by-product during production of chocolate, most of which is discarded in the present circumstances, and it is considered that use of the outer peel of cacao as a material is very excellent from a view of cost and a view of efficient utilization of resources.

According to the present invention, there are provided a substance having suppressing function for increase in blood cholesterol and foods and drinks in which it is used having function for decreasing blood pressure which are prepared from an albumen (including cocoa powder and the like) and/or an outer peel of cacao bean exactly as they are, or those after addition of physicochemical treatment or biochemical treatment, which are a substance and foods and drinks in which it is used giving no damage to the property of food and being capable of adding in a relatively large amount.

The LG-B1 and the LG-B2 according to the present invention contain lignin which is a phenolic polymer compound as a main component to have high cation exchange capacity, so that they absorb sodium ion to facilitate excretion. In addition, the LG-B1 and the LG-B2 according to the present invention do not damage the property of food being capable of taking in continuously.

Both of the LG-B1 and the LG-B2 according to the present invention are the acid-insoluble fraction extracted from wood materials, which have such a common characteristic that they contain lignin which is a phenolic polymer compound as a main component, so that they can be generally called as the LG fraction.

According to the result of epidemiological study on hypertension of Japanes people, it is known that cerebral hemorrhage in Japan is greatly affected by hypertension rather than lipid metabolism. As described above, taking the fact that the excess intake of common salt by Japanes people has hitherto been a problem into consideration, it is considered to be significant from a view of increasing health of national people that the LG-B1 and the LG-B2 according to the present invention facilitate excretion of sodium ion to suppress increase in blood pressure.

The LG-B1 and the LG-B2 according to the present invention have a high content of scarcely digestible fraction, containing lipid not more than about 10% respectively, being low in protein, containing sugar portion not more than 1%, also having such an advantage that they provide low energy.

They are those, the material of which is a natural food raw material having no limit for the amount of addition, which also has no hygroscopic property to be easy to add in a large amount to food from a view of food science.

According to the present invention, there are provided a substance having suppressing function for increase in blood pressure and foods and drinks in which it is used having function for decreasing blood pressure which are prepared from cacao (including an albumen, an outer peel, and cocoa powder after processing them) or other plant bodies (wood pulp, wood powder, straw, chaff, bran, bagasse and the like) exactly as they are, or those after addition of physicochemical treatment or biochemical treatment, which are a substance and foods and drinks in which it is used giving no damage to the property of food and being capable of adding continuously.

Both of the LG-C1 and the LG-C2 according to the present invention are the acid-insoluble fraction extracted from wood materials, which have such a common characteristic that they contain lignin which is a phenolic polymer compound as a main component, so that they can be generally called as the LG fraction.

As described above, cholesterol plays important roles in living bodies in such a way that it serves as a material for hormone, a composition for biomembranne and the like, which is not a useless bad one as such. However, in eating habits in the present age, it becomes a problem to take excess chlesterol.

However, in the prevention of the cholesterol gallstone, it is not sufficient that cholesterol in blood is simply decreased, but it is necessary that the balance with phospholipid is considered as an important factor. In addition, it is considered to be desirable that instead of those such as drugs having possibility of adverse effects, an effective substance without fear of adverse effects capable of routine intake is searched from natural substances.

Lignin which is a main component of the LG disclosed by the present invention, which is a kind of dietary fibre contained in a large amount in cocoa powder, Kiriboshi-daikon, chocolate and the like, is a food raw material for which a diet effect can be expected because it is difficult to be absorbed to provide no energy. These are those, the material of which is a natural food raw material having no limit for the amount of addition, which also has no adverse effect because of no absorption.

When pectin and alginic acid are added in foods, the physical property is easy to change due to the hygroscopic property and viscosity thereof, so that it is difficult to use in a large amount from a view of stability of food. And there are such disadvantages that the natural product of taurin requires high cost, and the unsaturated fatty acid provides high calorie. With respect to these points, the LG according to the present invention has no problem, which can be said as superior than other raw materials.

In addition, especially the outer peel of cacao is produced in a large amount as a by-product during production of chocolate, most of which is discarded in the present circumstances. And bagasse is waste of squeezing of cane, and also the straw and the chaff are usually disposed. It is considered that taking out of effective substances such as LG from them to apply to foods is very excellent from a view of cost and a view of efficient utilization of resources.

According to the present invention, there are provided a substance having suppressing function for cholesterol gallstone formation and foods and drinks in which it is used having suppressing function for cholesterol gallstone formation which are prepared from cacao (including an albumen, an outer peel, and cocoa powder after processing them) or other plant bodies (wood pulp, wood powder, straw, chaff, bran, bagasse and the like) exactly as they are, or those after addition of physicochemical treatment or biochemical treatment, which are a substance and foods and drinks in which it is used giving no damage to the property of food and being capable of adding in a relatively large amount.

The present invention will be further explained in detail according to examples hereinafter, however, the present invention is not limited only to the following examples.

EXAMPLE A1

PREPARATION OF LG-A1

To 30 g of cocoa powder was added 300 ml of a mixed liquid of chloroform: methanol (2:1), which were agitated for one hour to obtain degreased cocoa powder. To it was added 60 ml of 72% sulfuric acid to react for 2 hours with occasional agitation. 5000 ml of water was further added to perform reflux and heating for 4 hours. Filtration and washing were carried out, followed by drying to obtain 10 g of LG-A1.

Physicochemical characteristics of the obtained LG-A1 are those as mentioned hereinbefore.

EXAMPLE A2

Preparation of LG-A1

To 50 g of cacao husk (the outer peel of cacao bean) was added 500 ml of hexane, which was agitated for one hour to obtain degreased cacao husk. To it was added 1000 ml of 30% sulfuric acid to perform reflux and heating for one hour to filtrate to wash until the filtrate became neutral, after which lyophilization was carried out to obtain 10 g of LG-A1.

Physicochemical characteristics of the obtained LG-A1 are those as mentioned hereinbefore.

EXAMPLE A3

Preparation of LG-A2

To 50 g of cocoa powder was added 500 ml of ether, which was agitated for one hour to remove ether by filtration to obtain degreased cocoa powder. To it was added 1% sudium hydroxide aqueous solution to perform extraction at 80° C. for one hour. The extracted liquid was subjected to centrifugation to remove the solid content, after which adjustment to pH 5 was carried out, and centrifugation was further performed, and the precipitate was dried in an oven at 50° C. to obtain 12 g of LG-A2.

Physicochemical characteristics of the obtained LG-A2 are those as mentioned hereinbefore.

EXAMPLE A4

Example of experiment with animals

Rats having spontaneously fallen hypertension (SHR, male, 15 age in week, 7 individuals for each group) were preliminarily bred, after which they were bred with a semi-synthetic feed based on sucrose. SHR is a rat which suffers increase in plasma total cholesterol after changing to the feed based on sucrose. Blood collection was carried out from a tail of the rat on 10th day and 20th day. With respect to analysis, measurement was carried out using a Determiner TC555 made by Kyowa Medix by means of the enzyme method.

Results of the measurement for blood cholesterol are shown hereinafter. In addition, 7 individuals were used in the control group, and 7 individuals were used for 2% LG-A1 added group and 2% LG-A2 added group, and numerical values are shown as average values thereof. The unit is mg/dl. (LG-A1 and LG-A2 are those in which preparation procedure was changed.)

|  | Start | 10th day | 20th day |
| --- | --- | --- | --- |
| Control group | 60.6 | 126.3 | 145.8 |
| 2% LG-A1 added group | 61.3 | 97.0 | 102.1 |
| 2% LG-A2 added group | 62.2 | 109.4 | 112.3 |

According to the above result, it has been proved that the increase in plasma total cholesterol of SHR has been suppressed by addition of LG at 2% level.

EXAMPLE A5

Application to foods and drinks

Raw materials were blended according to the following formulation, and an LG-A1 added chocolate was produced according to the following procedure.

| | |
| --- | --- |
| Cacao mass | 15% |
| Powder sugar | 39% |
| Cacao butter | 18% |
| Whole milk powder | 20% |
| Skim milk powder | 5% |
| Lecithin | 0.3% |
| Spice | 0.1% |
| LG-A1 | 3.0% |

Parts of cacao butter and lecithin were mixed with raw materials other than spice with a mixer with monitoring viscosity. Next they were subjected to rolling so as to obtain a particle size not more than 40μ. To it were added the rest of cacao butter and lecithin and spice to perform conting to produce a chocolate dough. This was tempered, followed by pouring into a mold to solidify to produce a plate chocolate.

EXAMPLE A6

Application to food and drinks

Raw materials were blended according to the following formulation, and an LG-A2 added chocolate was produced according to the same procedure as Example A5.

| | |
| --- | --- |
| Cacao mass | 15% |
| Powder sugar | 39% |
| Cacao butter | 18% |
| Whole milk powder | 20% |
| Skim milk powder | 5% |
| Lecithin | 0.3% |
| Spice | 0.1% |
| LG-A2 | 3.0% |

COMPARATIVE TEST A1

Raw materials were blended according to the following formulation, and a pectin added chocolate was produced according to the same procedure as Example A5.

| | |
| --- | --- |
| Cacao mass | 15% |
| Powder sugar | 39% |
| Cacao butter | 18% |
| Whole milk powder | 20% |
| Skim milk powder | 5% |
| Lecithin | 0.3% |
| Spice | 0.1% |
| Pectin | 3.0% |

COMPARATIVE TEST A2

Raw materials were blended according to the following formulation, and a normal chocolate was produced according to the same procedure as Example A5.

| | |
|---|---|
| Cacao mass | 15% |
| Powder sugar | 42% |
| Cacao butter | 18% |
| Whole milk powder | 20% |
| Skim milk powder | 5% |
| Lecithin | 0.5% |
| Spice | 0.1% |

Eating trial for 4 kinds of chocolate produced as described above was carried out.

In the case of a plate chocolate of 100 g per one individual, when the LG added chocolates and the pectin added chocolate are compared with the normal chocolate, more dietary fibre can be taken in the LG added chocolates and the pectin added chocolate than the normal chocolate by about 3 g. Therefore, the suppressing effect for increase in blood cholesterol owing to the function of the dietary fibre can be obtained by the LG added chocolates and the pectin added chocolate.

However, in the pectin added chocolate, due to the influence of pectin, the viscosity of chocolate became high to worsen dissolution in mouth. On the contrary, the LG added chocolates according to the present invention provided a good taste which was not inferior to the normal chocolate also from a view of the taste.

EXAMPLE A7

Application to foods and drinks

Raw materials were blended according to the following formulation, and an LG-A1 added ring doughnut was produced according to the following procedure.

| | |
|---|---|
| Wheat flour | 31.2% |
| Sugar | 6.0% |
| Shortening | 1.0% |
| Margarine | 2.0% |
| Milk powder | 2.5% |
| Egg | 30% |
| Water | 20% |
| Yeast | 2.0% |
| Common salt | 0.4% |
| Yeast food | 0.2% |
| Emulsifier | 0.1% |
| Leavening agent | 1.5% |
| Spice | 0.1% |
| LG-A1 | 3% |

To wheat flour were added common salt, sugar, fats, yeast, dairy products, egg, and water, and mixing was carried out to make a dough. At this time, yeast food for aiding fermentation, emulsifier, leavening agent, and spice were also added. Next the dough was subjected to sufficient fermentation, and divided to shape to be a ring form. Final fermentation was further carried out to fry by a fryer to make a product.

EXAMPLE A8

Application to foods and drinks

Raw materials were blended according to the following formulation, and an LG-A2 added ring doughnut was produced according to the same procedure as Example A7.

| | |
|---|---|
| Wheat flour | 31.2% |
| Sugar | 6.0% |
| Shortening | 1.0% |
| Margarine | 2.0% |
| Milk powder | 2.5% |
| Egg | 30% |
| Water | 20% |
| Yeast | 2.0% |
| Common salt | 0.4% |
| Yeast food | 0.2% |
| Emulsifier | 0.1% |
| Leavening agent | 1.5% |
| Spice | 0.1% |
| LG-A2 | 3% |

COMPARATIVE TEST A3

Raw materials were blended according to the following formulation, and a pectin added ring doughnut was produced according to the same procedure as Example A7.

| | |
|---|---|
| Wheat flour | 31.2% |
| Sugar | 6.0% |
| Shortening | 1.0% |
| Margarine | 2.0% |
| Milk powder | 2.5% |
| Egg | 30% |
| Water | 20% |
| Yeast | 2.0% |
| Common salt | 0.4% |
| Yeast food | 0.2% |
| Emulsifier | 0.1% |
| Leavening agent | 1.5% |
| Spice | 0.1% |
| Pectin | 3.0% |

COMPARATIVE TEST A4

Raw materials were blended according to the following formulation, and an EPA added ring doughnut was produced according to the same procedure as Example A7.

| | |
|---|---|
| Wheat flour | 34.2% |
| Sugar | 6.0% |
| Shortening | 0.5% |
| Margarine | 1.5% |
| Milk powder | 2.5% |
| Egg | 30% |
| Water | 20% |
| Yeast | 2.0% |
| Common salt | 0.4% |
| Yeast food | 0.2% |
| Emulsifier | 0.1% |
| Leavening agent | 1.5% |
| Spice | 0.1% |
| EPA | 1.0% |

COMPARATIVE TEST A5

Raw materials were blended according to the following formulation, and a normal ring doughnut was produced according to the same procedure as Example A7.

| | |
|---|---|
| Wheat flour | 34.2% |
| Sugar | 6.0% |
| Shortening | 1.0% |
| Margarine | 2.0% |
| Milk powder | 2.5% |
| Egg | 30% |

| | |
|---|---|
| -continued | |
| Water | 20% |
| Yeast | 2.0% |
| Common salt | 0.4% |
| Yeast food | 0.2% |
| Emulsifier | 0.1% |
| Leavening agent | 1.5% |
| Spice | 0.1% |

Eating trial for 5 kinds of ring doughnuts produced as described above was carried out.

In the case of a ring doughnut of 100 g by two individuals, when the LG added ring doughnuts and the pectin added ring doughnut are compared with the normal ring doughnut, more dietary fibre can be taken in the LG added ring doughnuts and the pectin added ring doughnut than the normal ring doughnut by about 3 g. Therefore, the suppressing effect for increase in blood cholesterol owing to the function of the dietary fibre can be obtained by the LG added ring doughnuts and the pectin added ring doughnut.

However, in the pectin added ring doughnut, such problems took place that the viscosity of the ring doughnut dough became high due to the influence of pectin resulting in insufficient fermentation and becoming hygroscopic during storage. On the contrary, the LG added ring doughnuts according to the present invention provided a good taste which was not inferior to the normal ring doughnut also from a view of the taste.

The EPA added ring doughnut had a strong fish odor probably because a crude EPA was used, in which a distinct flavor of a ring doughnut was hidden, resulting in an extremely low taste.

EXAMPLE B1

Preparation of LG-B1

To 50 g of cacao husk was added 500 ml of hexane, which were agitated for one hour to obtain degreased cacao husk. To it was added 1000 ml of 30% sulfuric acid to perform reflux and heating for one hour to filtrate, and washing was carried out until the filtrate became neutral, followed by lyophilization to obtain 10 g of LG-B1.

Physicochemical characteristics of the obtained LG-B1 are those as mentioned hereinbefore.

EXAMPLE B2

Preparation of LG-B1

To 30 g of wood powder of a white birch was added 300 ml of hexane, which was agitated for one hour to obtain degreased wood powder of a white birch. To it was added 60 ml of 72% sulfuric acid to react for 2 hours with occasional agitation. And 5000 ml of water was further added to perform reflux and heating for 4 hours. Drying was carried out after filtration and washing to obtain about 12 g of LG-B1.

Physicochemical characteristics of the obtained LG-B1 are those as mentioned hereinbefore.

EXAMPLE B3

Preparation of LG-B2

To 50 g of cocoa powder was added 500 ml of hexane, which was agitated for one hour to remove hexane by filtration to obtain degreased cocoa powder. To it was added 1% sudium hydroxide aqueous solution to perform extraction at 80° C. for one hour. The extracted liquid was subjected to centrifugation to remove the solid content, after which adjustment to pH 5 was carried out, and centrifugation was further performed, and the precipitate was dried in an oven at 50° C. to obtain 12 g of LG-B2.

Physicochemical characteristics of the obtained LG-B2 are those as mentioned hereinbefore.

EXAMPLE B4

Example of experiment with animals

Rats having spontaneously fallen hypertension (SHR, male, 15 age in week, 7 individuals for each group) were preliminarily bred, after which they were bred with a semi-synthetic feed based on sucrose containing 1% common salt. SHR is a rat which suffers increase in blood pressure after changing to the feed based on sucrose. In various LG groups, sucrose in the control group was changed by various LG's of about 3%. Blood pressure was measured by every 7 days without observing blood by a rat tail arteria blood pressure measuring apparatus PS-100.

Results of the measurement for blood pressure are shown hereinafter. In addition, numerical values are average values of 7 individuals of each group, and the unit is mmHg.

| | Start | 7th day | 14th day | 21th day |
|---|---|---|---|---|
| Control group | 200.4 | 208.7 | 209.8 | 210.7 |
| Cacao LG-B1 group | 200.1 | 192.5 | 190.3 | 186.8 |
| Cacao LG-B2 group | 199.3 | 193.2 | 188.3 | 186.3 |
| White birch LG | 192.6 | 192.7 | 191.3 | 187.9 |

According to the above result, it has been proved that the increase in blood pressure of SHR has been suppressed by various LG's.

In addition, changes in sodium excresion to feces at this time are shown hereinafter. Here, the unit is the number of mg of Na in 1 g of feces.

| | Na excrestion amount |
|---|---|
| Control | 7.9 |
| Cacao LG-B1 group | 15.3 |
| Cacao LG-B2 group | 19.2 |
| White birch LG | 18.6 |

According to the results, it can be seen that the sodium excretion amount increased on account of various LG's.

EXAMPLE B5

Application to foods and drinks

Raw materials were blended according to the following formulation, and an LG-B1 added chocolate was produced according to the following procedure.

| | |
|---|---|
| Cacao mass | 15% |
| Powder sugar | 39% |
| Cacao butter | 18% |
| Whole milk powder | 20% |
| Skim milk powder | 5% |
| Lecithin | 0.3% |
| Spice | 0.1% |
| LG-B1 | 3.0% |

Parts of cacao butter and lecithin were mixed with raw materials other than spice with a mixer with monitoring viscosity. Next they were subjected to rolling so as to obtain a particle size not more than 40μ. To it were added the rest of cacao butter and lecithin and spice to perform conting to produce a chocolate dough. This was tempered, followed by pouring into a mold to solidify to produce a plate chocolate.

EXAMPLE B6

Application to foods and drinks

Raw materials were blended according to the following formulation, and an LG-B2 added chocolate was produced according to the same procedure as Example B5.

| Cacao mass | 15% |
| --- | --- |
| Powder sugar | 39% |
| Cacao butter | 18% |
| Whole milk powder | 20% |
| Skim milk powder | 5% |
| Lecithin | 0.3% |
| Spice | 0.1% |
| LG-B2 | 3.0% |

COMPARATIVE TEST B1

Raw materials were blended according to the following formulation, and an alginic acid added chocolate was produced according to the same procedure as Example B5.

| Cacao mass | 15% |
| --- | --- |
| Powder sugar | 39% |
| Cacao butter | 18% |
| Whole milk powder | 20% |
| Skim milk powder | 5% |
| Lecithin | 0.3% |
| Spice | 0.1% |
| Alginic acid | 3.0% |

COMPARATIVE TEST B2

Raw materials were blended according to the following formulation, and a normal chocolate was produced according to the same procedure as Example B5.

| Cacao mass | 15% |
| --- | --- |
| Powder sugar | 42% |
| Cacao butter | 18% |
| Whole milk powder | 20% |
| Skim milk powder | 5% |
| Lecithin | 0.5% |
| Spice | 0.1% |

Eating trial for 4 kinds of chocolate produced as described above was carried out.

In the case of a plate chocolate of 100 g per one individual, when the LG added chocolates and the alginic acid added chocolate are compared with the normal chocolate, more dietary fibre can be taken in the LG added chocolate and the alginic acid added chocolate than the normal chocolate by about 3 g. Therefore, the suppressing effect for increase in blood pressure owing to the function of the dietary fibre can be obtained by the LG added chocolates and the alginic acid added chocolate.

However, in the alginic acid added chocolate, due to the influence of alginic acid, the viscosity of chocolate became high to worsen dissolution in mouth. On the contrary, the LG added chocolates according to the present invention provided a good taste which was not inferior to the normal chocolate also from a view of the taste.

Moreover, in the LG added chocolate according to the present invention, the increasing effect in the sodium excretion amount can be obtained owing to the absorption function for sodium ion on account of the high cation exchange capacity.

EXAMPLE B7

Application to foods and drinks

Raw materials were blended according to the following formulation, and an LG-B1 added ring doughnut was produced according to the following procedure.

| Wheat flour | 31.2% |
| --- | --- |
| Sugar | 6.0% |
| Shortening | 1.0% |
| Margarine | 2.0% |
| Milk powder | 2.5% |
| Egg | 30% |
| Water | 20% |
| Yeast | 2.0% |
| Common salt | 0.4% |
| Yeast food | 0.2% |
| Emulsifier | 0.1% |
| Leavening agent | 1.5% |
| Spice | 0.1% |
| LG-B1 | 3% |

To wheat flour were added common salt, sugar, fats, yeast, dairy products, egg, and water, and mixing was carried out to make a dough. At this time, yeast food for aiding fermentation, emulsifier, leavening agent, and spice were also added. Next the dough was subjected to sufficient fermentation, and divided to shape to be a ring form. Final fermentation was further carried out to fry by a fryer to make a product.

EXAMPLE B8

Application to foods and drinks

Raw materials were blended according to the following formulation, and an LG-B2 added ring doughnut was produced according to the same procedure as Example B7.

| Wheat flour | 31.2% |
| --- | --- |
| Sugar | 6.0% |
| Shortening | 1.0% |
| Margarine | 2.0% |
| Milk powder | 2.5% |
| Egg | 30% |
| Water | 20% |
| Yeast | 2.0% |
| Common salt | 0.4% |
| Yeast food | 0.2% |
| Emulsifier | 0.1% |
| Leavening agent | 1.5% |
| Spice | 0.1% |
| LG-B2 | 3% |

COMPARATIVE TEST B3

Raw materials were blended according to the following formulation, and an alginic acid added ring doughnut was produced according to the same procedure as Example B7.

| Wheat flour | 31.2% |
| --- | --- |

-continued

| | |
|---|---|
| Sugar | 6.0% |
| Shortening | 1.0% |
| Margarine | 2.0% |
| Milk powder | 2.5% |
| Egg | 30% |
| Water | 20% |
| Yeast | 2.0% |
| Common salt | 0.4% |
| Yeast food | 0.2% |
| Emulsifier | 0.1% |
| Leavening agent | 1.5% |
| Spice | 0.1% |
| Alginic acid | 3.0% |

COMPARATIVE TEST B4

Raw materials were blended according to the following formulation, and a normal ring doughnut was produced according to the same procedure as Example B7.

| | |
|---|---|
| Wheat flour | 34.2% |
| Sugar | 6.0% |
| Shortening | 1.0% |
| Margarine | 2.0% |
| Milk powder | 2.5% |
| Egg | 30% |
| Water | 20% |
| Yeast | 2.0% |
| Common salt | 0.4% |
| Yeast food | 0.2% |
| Emulsifier | 0.1% |
| Leavening agent | 1.5% |
| Spice | 0.1% |

Eating trial for 4 kinds of ring doughnuts produced as described above was carried out.

In the case of a ring doughnut of 100 g by two individuals, when the LG added ring doughnuts and the alginic acid added ring doughnut are compared with the normal ring doughnut, more dietary fibre can be taken in the LG added ring doughnuts and the alginic acid added ring doughnut than the normal ring doughnut by about 3 g. Therefore, the suppressing effect for increase in blood pressure owing to the function of the dietary fibre can be obtained by the LG added ring doughnuts and the alginic acid added ring doughnut.

However, in the alginic acid added ring doughnut, such problems took place that the viscosity of the ring doughnut dough became high due to the influence of alginic acid resulting in insufficient fermentation and becoming hygroscopic during storage. On the contrary, the LG added ring doughnuts according to the present invention provided a good taste which was not inferior to the normal ring doughnut also from a view of the taste.

EXAMPLE C1

Preparation of LG-C1

To 30 g of wood powder of a white birch was added 300 ml of a mixed liquid of chlorform: methanol (2:1), which were agitated for one hour to obtain degreased wood powder of a white birch. To it was added 60 ml of 72% sulfuric acid to react for 2 hours with occasional agitation. 5000 ml of water was further added to perform reflux and heating for 4 hours. Filtration and washing were carried out, followed by drying to obtain about 12 g of LG-C1.

Physicochemical characteristics of the obtained LG-C1 are those as mentioned hereinbefore.

EXAMPLE C2

Preparation of LG-C1

To 50 g of cacao husk (the outer peel of cacao bean) was added 500 ml of hexane, which was agitated for one hour to obtain degreased cacao husk. To it was added 1000 ml of 30% sulfuric acid to perform reflux and heating for one hour to filtrate to wash until the filtrate became neutral, after which lyophilization was carried out to obtain 10 g of LG-C1.

Physicochemical characteristics of the obtained LG-C1 are those as mentioned hereinbefore.

EXAMPLE C3

Preparation of LG-C2

To 50 g of cocoa powder was added 500 ml of ether, which was agitated for one hour to remove ether by filtration to obtain degreased cocoa powder. To it was added 1% sudium hydroxide aqueous solution to perform extraction at 80° C. for one hour. The extracted liquid was subjected to centrifugation to remove the solid content, after which adjustment to pH 5 was carried out, and centrifugation was further performed, and the precipitate was dried in an oven at 50° C. to obtain 12 g of LG-C2.

Physicochemical characteristics of the obtained LG-C2 are those as mentioned hereinbefore.

EXAMPLE C4

Example of experiment with animals

Rats of the LCR type (5 age in week, 15 individuals for each group) were preliminarily bred, after which they were bred with a semi-synthetic feed containing 0.5% cholesterol and 0.25% sodium cholate for 5 weeks (as a control group was provided a feed group in which cholesterol and sodium cholate were not contained). To experiment groups was added LG prepared from various samples by about 3% (sucrose in the control feed was replaced). After completion of breeding, the head-cut and anatomy were carried out to take out the cholecyst, and observation was performed by human eyes to confirm the presence or the absence of gallstone.

The results of the presence or the absence of gallstone formation are shown as follows.

| | Generation number | Generation ratio |
|---|---|---|
| No addition of cholesterol | 0/15 individuals | 0% |
| Cholesterol loaded group | 15/15 individuals | 100% |
| Cacao LG-C1 added group | 10/15 individuals | 66% |
| Cacao LG-C2 added group | 13/15 individuals | 86% |
| Wood LG added group | 9/15 individuals | 60% |
| Bagasse LG added group | 8/15 individuals | 53% |

According to the above result, it is understood that the cholesterol gallstone formation has been suppressed by adding various LG's.

EXAMPLE C5

Application to foods and drinks

Raw materials were blended according to the following formulation, and an LG-C1 added chocolate was produced according to the following procedure.

| Cacao mass | 15% |
|---|---|
| Powder sugar | 39% |
| Cacao butter | 18% |
| Whole milk powder | 20% |
| Skim milk powder | 5% |
| Lecithin | 0.3% |
| Spice | 0.1% |
| LG-C1 | 3.0% |

Parts of cacao butter and lecithin were mixed with raw materials other than spice with a mixer with monitoring viscosity. Next they were subjected to rolling so as to obtain a particle size not more than 40μ. To it were added the rest of cacao butter and lecithin and spice to perform conting to produce a chocolate dough. This was tempered, followed by pouring into a mold to solidify to produce a plate chocolate.

EXAMPLE C6

Application to foods and drinks

Raw materials were blended according to the following formulation, and an LG-C2 added chocolate was produced according to the same procedure as Example C5.

| Cacao mass | 15% |
|---|---|
| Powder sugar | 39% |
| Cacao butter | 18% |
| Whole milk powder | 20% |
| Skim milk powder | 5% |
| Lecithin | 0.3% |
| Spice | 0.1% |
| LG-C2 | 3.0% |

COMPARATIVE TEST C1

Raw materials were blended according to the following formulation, and a pectin added chocolate was produced according to the same procedure as Example C5.

| Cacao mass | 15% |
|---|---|
| Powder sugar | 39% |
| Cacao butter | 18% |
| Whole milk powder | 20% |
| Skim milk powder | 5% |
| Lecithin | 0.3% |
| Spice | 0.1% |
| Pectin | 3.0% |

COMPARATIVE TEST C2

Raw materials were blended according to the following formulation, and an EPA added chocolate was produced according to the same procedure as Example C5.

| Cacao mass | 15% |
|---|---|
| Powder sugar | 41% |
| Cacao butter | 18% |
| Whole milk powder | 20% |
| Skim milk powder | 5% |
| Lecithin | 0.3% |
| Spice | 0.1% |
| EPA | 1.0% |

COMPARATIVE TEST C3

Raw materials were blended according to the following formulation, and a normal chocolate was produced according to the same procedure as Example C5.

| Cacao mass | 15% |
|---|---|
| Powder sugar | 42% |
| Cacao butter | 18% |
| Whole milk powder | 20% |
| Skim milk powder | 5% |
| Lecithin | 0.5% |
| Spice | 0.1% |

Eating trial for 5 kinds of chocolate produced as described above was carried out.

In the case of a plate chocolate of 100 g per one individual, when the LG added chocolates and the pectin added chocolate are compared with the normal chocolate, more dietary fibre can be taken in the LG added chocolates and the pectin added chocolate than the normal chocolate by about 3 g. Therefore, the suppressing effect for cholesterol gallstone formation owing to the function of the dietary fibre can be obtained by the LG added chocolates and the pectin added chocolate.

However, in the pectin added chocolate, due to the influence of pectin, the viscosity of chocolate became high to worsen dissolution in mouth. On the contrary, the LG added chocolates according to the present invention provided a good taste which was not inferior to the normal chocolate also from a view of the taste.

The EPA added chocolate had a strong fish odor probably because a crude EPA was used, in which a distinct flavor of a chocolate was hidden, resulting in a low taste.

EXAMPLE C7

Application to foods and drinks

Raw materials were blended according to the following formulation, and an LG-C1 added ring doughnut was produced according to the following procedure.

| Wheat flour | 31.2% |
|---|---|
| Sugar | 6.0% |
| Shortening | 1.0% |
| Margarine | 2.0% |
| Milk powder | 2.5% |
| Egg | 30% |
| Water | 20% |
| Yeast | 2.0% |
| Common salt | 0.4% |
| Yeast food | 0.2% |
| Emulsifier | 0.1% |
| Leavening agent | 1.5% |
| Spice | 0.1% |
| LG-C1 | 3% |

To wheat flour were added common salt, sugar, fats, yeast, dairy products, egg, and water, and mixing was carried out to make a dough. At this time, yeast food for aiding fermentation, emulsifier, leavening agent, and spice were also added. Next the dough was subjected to sufficient fermentation, and divided to shape to be a ring form. Final fermentation was further carried out to fry by a fryer to make a product.

EXAMPLE C8

Application to Foods and Drinks

Raw materials were blended according to the following formulation, and an LG-C2 added ring doughnut was produced according to the same procedure as Example C7.

| | |
|---|---|
| Wheat flour | 31.2% |
| Sugar | 6.0% |
| Shortening | 1.0% |
| Margarine | 2.0% |
| Milk powder | 2.5% |
| Egg | 30% |
| Water | 20% |
| Yeast | 2.0% |
| Common salt | 0.4% |
| Yeast food | 0.2% |
| Emulsifier | 0.1% |
| Leavening agent | 1.5% |
| Spice | 0.1% |
| LG-C2 | 3% |

COMPARATIVE TEST C4

Raw materials were blended according to the following formulation, and a pectin added ring doughnut was produced according to the same procedure as Example C7.

| | |
|---|---|
| Wheat flour | 31.2% |
| Sugar | 6.0% |
| Shortening | 1.0% |
| Margarine | 2.0% |
| Milk powder | 2.5% |
| Egg | 30% |
| Water | 20% |
| Yeast | 2.0% |
| Common salt | 0.4% |
| Yeast food | 0.2% |
| Emulsifier | 0.1% |
| Leavening agent | 1.5% |
| Spice | 0.1% |
| Pectin | 3.0% |

COMPARATIVE TEST C5

Raw materials were blended according to the following formulation, and an EPA added ring doughnut was produced according to the same procedure as Example C7.

| | |
|---|---|
| Wheat flour | 34.2% |
| Sugar | 6.0% |
| Shortening | 0.5% |
| Margarine | 1.5% |
| Milk powder | 2.5% |
| Egg | 30% |
| Water | 20% |
| Yeast | 2.0% |
| Common salt | 0.4% |
| Yeast food | 0.2% |
| Emulsifier | 0.1% |
| Leavening agent | 1.5% |
| Spice | 0.1% |
| EPA | 1.0% |

COMPARATIVE TEST C6

Raw materials were blended according to the following formulation, and a normal ring doughnut was produced according to the same procedure as Example C7.

| | |
|---|---|
| Wheat flour | 34.2% |
| Sugar | 6.0% |
| Shortening | 1.0% |
| Margarine | 2.0% |
| Milk powder | 2.5% |
| Egg | 30% |
| Water | 20% |
| Yeast | 2.0% |
| Common salt | 0.4% |
| Yeast food | 0.2% |
| Emulsifier | 0.1% |
| Leavening agent | 1.5% |
| Spice | 0.1% |

Eating trial for 5 kinds of ring doughnuts produced as described above was carried out.

In the case of a ring doughnut of 100 g by two individuals, when the LG added ring doughnuts and the pectin added ring doughnut are compared with the normal ring doughnut, more dietary fibre can be taken in the LG added ring doughnuts and the pectin added ring doughnut than the normal ring doughnut by about 3 g. Therefore, the suppressing effect for cholesterol gallstone formation owing to the function of the dietary fibre can be obtained by the LG added ring doughnuts and the pectin added ring doughnut.

However, in the pectin added ring doughnut, such problems took place that the viscosity of the ring doughnut dough became high due to the influence of pectin resulting in insufficient fermentation and becoming hygroscopic during storage. On the contrary, the LG added ring doughnuts according to the present invention provided a good taste which was not inferior to the normal ring doughnut also from a view of the taste.

The EPA added ring doughnut had a strong fish odor probably because a crude EPA was used, in which a distinct flavor of a ring doughnut was hidden, resulting in an extremely low taste.

What is claimed is:

1. A substance having suppressing functions for disorders relating to increase in cholesterol in mammals, said substance being obtained as an acid-insoluble fraction containing lignin from plant material to which has been added sulfuric acid of a concentration of 40-98% and a volume of 2-10 times the volume of said material to hydrolyze said material, followed by separation of liquid from solid material, washing of the solid material to neutralize the solid material, and drying of the solid material, said solid material comprising said substance and having the following physicochemical characteristics:

molecular weight: not less than 200,
    sugar content: not more than 1%,
    nitrogen content: 1.5 to 5.5%,
    fat content: not more than 10%,
    ash content: not more than 10%, and
    methoxy content: 5 to 40%.

2. A substance as claimed in claim 1, in which said plant material is cacao husk.

3. A substance as claimed in claim 1, in which said plant material is cocoa powder.

4. A substance as claimed in claim 1, in which said plant material is wood powder.

5. A food stuff containing a substance as claimed in claim 1 admixed therein.

6. A substance having suppressing functions for disorders relating to increase in cholesterol in mammals, said substance being obtained as an acid-insoluble fraction containing lignin from plant material to which has been added alkali hydroxide of a concentration of 0.1-2.0% to said material in a volume of 10-50 times, letting stand the mixture of said hydroxide and said material not less than 30 minutes, separating solids from said mixture of alkali hydroxide and plant material to leave a liquid, neutralizing said liquid to generate a precipitate, removing liquid from said precipitate and washing and drying said precipitate, said precipitate comprising said substance and having the following physicochemical characteristics:

molecular weight: not less than 200,
sugar content: not more than 1%,
nitrogen content: 1.5 to 5.5%,
fat content: not more than 10%,
ash content: not more than 10%, and
methoxy content: 5 to 40%.

7. A substance as claimed in claim 6, in which said plant material is cacao husk.

8. A substance as claimed in claim 6, in which said plant material is cocoa powder.

9. A substance as claimed in claim 6, in which said plant material is wood powder.

10. A food stuff containing a substance as claimed in claim 6 admixed therein.

* * * * *